United States Patent [19]

Laurichesse et al.

[11] Patent Number: 4,824,370
[45] Date of Patent: Apr. 25, 1989

[54] DENTAL DRILL

[75] Inventors: Jean M. Laurichesse, Paris; Henri Leonard, Besancon, both of France

[73] Assignee: Micro-Mega, Besancon, France

[21] Appl. No.: 237,660

[22] Filed: Aug. 25, 1988

Related U.S. Application Data

[63] Continuation of Ser. No. 70,090, Jul. 6, 1987, abandoned, Continuation of Ser. No. 799,359, Nov. 18, 1985, abandoned.

[30] Foreign Application Priority Data

Jan. 11, 1985 [FR] France .................. 85 00485

[51] Int. Cl.$^4$ .............................................. A61C 5/02
[52] U.S. Cl. ................................................. 433/102
[58] Field of Search ....................................... 433/102

[56] References Cited

U.S. PATENT DOCUMENTS

| | | | |
|---|---|---|---|
| 322,265 | 7/1885 | Donaldson | 433/102 |
| 717,594 | 1/1903 | Miles et al. | 433/102 |
| 4,538,989 | 9/1985 | Apairo et al. | 433/102 |

FOREIGN PATENT DOCUMENTS 478886 12/1927 Fed. Rep. of Germany ...... 433/102

Primary Examiner—Robert Peshock
Attorney, Agent, or Firm—Emmanuel J. Lobato; Robert E. Burns

[57] ABSTRACT

A dental drill having an elongate drill body tapered to a conical tip. The drill body has a plurality of substantially identical barbs projecting outwardly from the drill body and arranged helically about the drill body. Each barb has an outer peripheral profile resembling a parabola in shape extending generally toward the tip of the drill body. Each barb has a flat surface contiguous with the flat surface of an adjacent barb at a point of juncture with the drill body. The barb flat surfaces are disposed in a common helical path about the drill body and each has a shape resembling a parabola. The barbs have a peripheral profile also resembling a parabola. Each resembles a paraboloid in which intersections by planes parallel to the corresponding flat surface thereof and spaced axially on the drill body resemble parabolas with the axes thereof decreasing in length as the intersections are made in a direction toward the tip of the drill body.

5 Claims, 2 Drawing Sheets

DENTAL DRILL

This is a continuation of application Ser. No. 07/070,090, filed July 6, 1987 and now abandoned, which is a continuation of application Ser. No. 06/799,359 filed Nov. 18, 1985, now abandoned.

The present invention concerns an improvement for dental instruments of the boring type, and especially tooth drills consisting in a conical rod on which have been made, by pushing the metal, e.g. with a chisel, bumps or barbs helicoidally running around the rod with a progressive pitch from the point towards the handle.

These tooth drills are fully satisfactory, but, in certain cases, still may have certain inconveniences, linked to the way the barbs are made.

Indeed, the barbs are usually obtained by scraping a chisel parallel to the axis of the rod, in such a way that, the rod being conical, the barbs are not identical to each other, but, to the contrary, they are less and less pronounced from the point towards the handle.

This irregularity has at least two consequences. The first is that the longer barbs that push against the dentin may stick into it and be torn from the rod, and this would leave metal fragments in the duct. The second is that the pushing back of the metal in the thickest part of the rod causes an indentation of the rod and makes this zone the most fragile part of it.

Finally, the way the barbs are spaced out makes them too far from each other, which is also detrimental to the efficiency of the instrument.

The invention focuses on a drill of this type, but without the inconveniences, thanks to a different kind of fabrication.

According to the invention, the barbs are made by a chisel moving in a direction that is at a angle with the axis of the rod equal to the inclination of the helicoidal path on which the barbs are spaced out. This has for effect to lift up the barbs that are very close to each other, very small and all of the same size, and eliminates the defects mentioned above.

The characteristics of the invention will now be described in more detail, in comparison with previous techniques, referring to the annexed drawing, in which:

FIG. 3 is a cut-off following III—III of FIG. 2, while

DESCRIPTION OF THE PREFERRED EMBODIMENT

Figure 2:
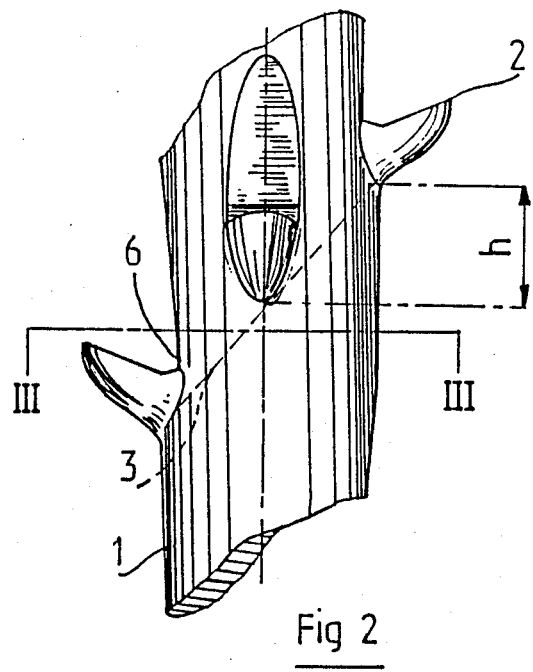
FIG. 2 is a partial enlarged view of FIG. 1.
Figure 3:
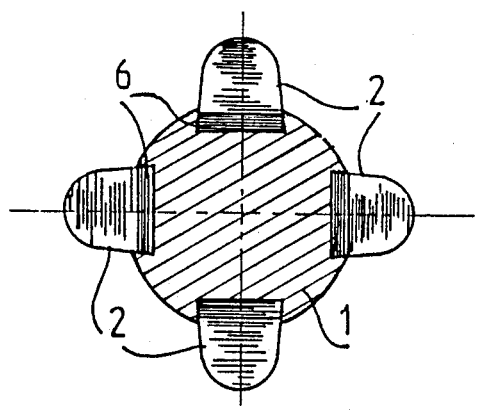
Figure 1:
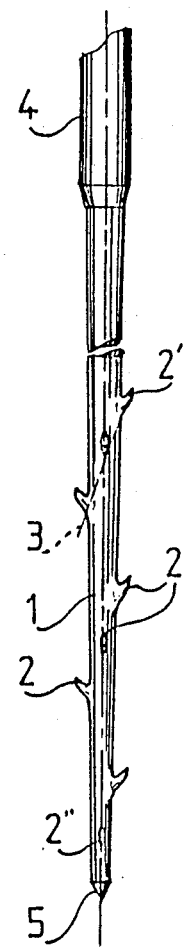
FIG. 1 shows a barbed drill according to the the previous technique.

Referring first to FIGS. 1 to 3, a drill is shown consisting in a vertical conical drum, the material of which has been scraped with a chisel moving vertically in order to form the barbs 2. From one barb to the other, the drum moves at a height h turning at 90°, so that all of the barbs are spaced out along a helicoidal path 3 that follows four generatrices equidistant from the cone, as best seen in FIG. 3.

Figure 5:
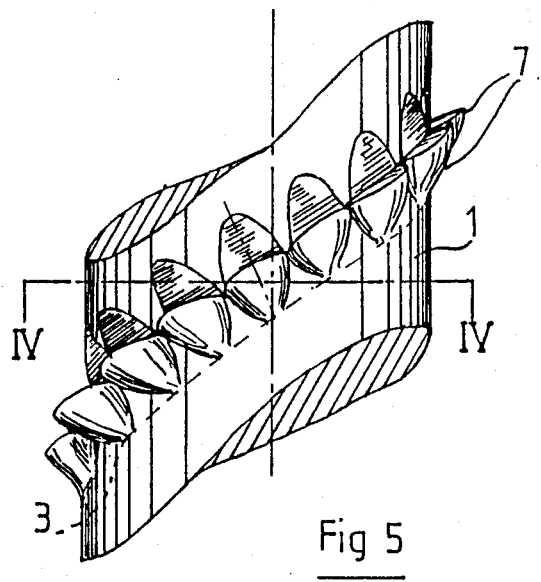
FIGS. 4, 5 and 6 are the corresponding views of the drill according to the invention.
Figure 4:
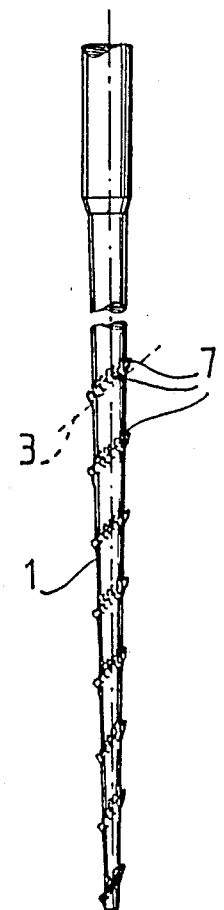
Figure 6:
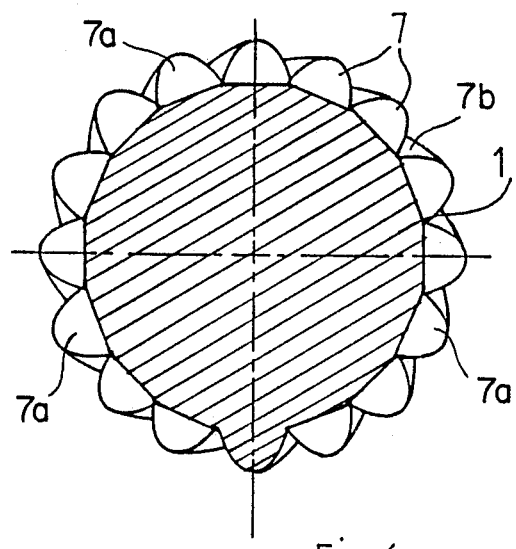

Since the chisel is used vertically, it is clear that the barbs 2' near the end 4 of the rod will be smaller than the barbs 2" near the point 5. The longer barbs 5" are the most likely to break off by remaining stuck in the dentin of the duct. Moreover, the scraping of the metal makes indentations 6 on the drum (FIG. 2) rendering these zones fragile. Referring now to FIGS. 4 to 6, one can see that, on the conical drum 1, the chisel (not shown) scrapes the material in a direction at an angle $\alpha$ with the axis of the rod, making very close identical barbs 7 that are also spaced out on the helicoidal path 3.

This mechanism has the advantage of creating bumps that are very close to each other, but leaving smooth a part of the supporting rod between their paths.

Such an instrument is very efficient for an effective scraping of the dentin without the inconveniences mentioned above, and the shavings that are taken out have more room in the parts that have not yet been scraped. Moreover, the scraped surface obtained with this instrument is smooth, because the barbs are very close together.

As illustrated in the drawing and described above the dental drill 1 has an elongate drill body tapered to a conical tip. The barbs each have an outer profile resembling a parabola in shape extending generally toward the tip. Each barb has a flat surface 7a contiguous to an adjacent barb flat surface 7a at the points of juncture 7b to the drill body. Each of the flat surfaces 7a has a shape resembling a parabola projecting outwardly from the drill body along a helical path. Crossections of the individual barbs defined by intersections by planes parallel to the corresponding flat surface and spaced axially on the drill body resemble parabolas with axes thereof decreasing in length as the intersections are made by the axial planes in a direction toward said tip.

This instrument can be used by hand to bore the ducts, as well as in the subsonic vibration devices described in the French Pat. No. 82/18545 of the claimant.

We claim:

1. A dental drill comprising, a tip, an elongate drill body tapered to said tip, said drill body having a plurality of barbs projecting outwardly from the drill body and arranged helically about the drill body, the barbs each having an outer peripheral profile resembling a parabola in shape extending generally toward said tip, each barb having a flat surface contiguous with a corresponding flat surface of an adjacent barb, each flat surface of the barbs being disposed in a common helical path about the drill body and each having a shape resembling a parabola projecting outwardly from the drill body, and each barb having a shape resembling a paraboloid in which crossections defined by intersections by planes parallel to the corresponding flat surface thereof and spaced axially on the drill body resemble parabolas with axes thereof decreasing in length as the intersections are made in a direction toward said tip.

2. A dental drill according to claim 1, in which said common helical path has a constant pitch.

3. A dental drill according to claim 1, in which said tip is conical.

4. A dental drill according to claim 1, in which each flat surface of a corresponding barb is contiguous to adjacent flat surfaces at points of juncture to the drill body.

5. A dental drill according to claim 1, in which said barbs are substantially identical.

* * * * *